United States Patent [19]
Walker

[11] 4,028,819
[45] June 14, 1977

[54] METHOD FOR MEASURING TASKS AND MEANS FOR GENERATING COORDINATED AUDIO-VISUAL STIMULI AND ERROR INDICIA FOR SAID SECONDARY TASKS

[76] Inventor: Norman K. Walker, 6613 Sulky Lane, Rockville, Md. 20852

[22] Filed: July 12, 1974

[21] Appl. No.: 488,072

[52] U.S. Cl. .............................................. 35/22 R
[51] Int. Cl.² ....................................... G09B 19/00
[58] Field of Search .......... 35/22 R, 12 D; 128/2 R

[56] References Cited
UNITED STATES PATENTS

| | | | |
|---|---|---|---|
| 1,564,138 | 12/1925 | Rowland | 35/22 R X |
| 2,023,488 | 12/1935 | Poppen | 35/22 R X |
| 2,341,678 | 2/1944 | Wickes | 35/22 R X |
| 3,357,115 | 12/1967 | Kelley | 35/22 R |
| 3,579,865 | 5/1971 | Walker | 35/22 R |

*Primary Examiner*—William H. Grieb
*Attorney, Agent, or Firm*—Birch, Stewart, Kolasch & Birch

[57] ABSTRACT

An improved method and apparatus for measuring the effects of stress on a person's performance of a primary task, while a secondary task is also provided to be performed simultaneously by the test subject and the results of such measurements providing parameters for diagnosing various physiological and mental disorders. A multiple mode and variable format secondary task command stimulus generator is provided which detects the lack of and/or correctness of the response of the test subject to the secondary task command stimuli.

11 Claims, 3 Drawing Figures

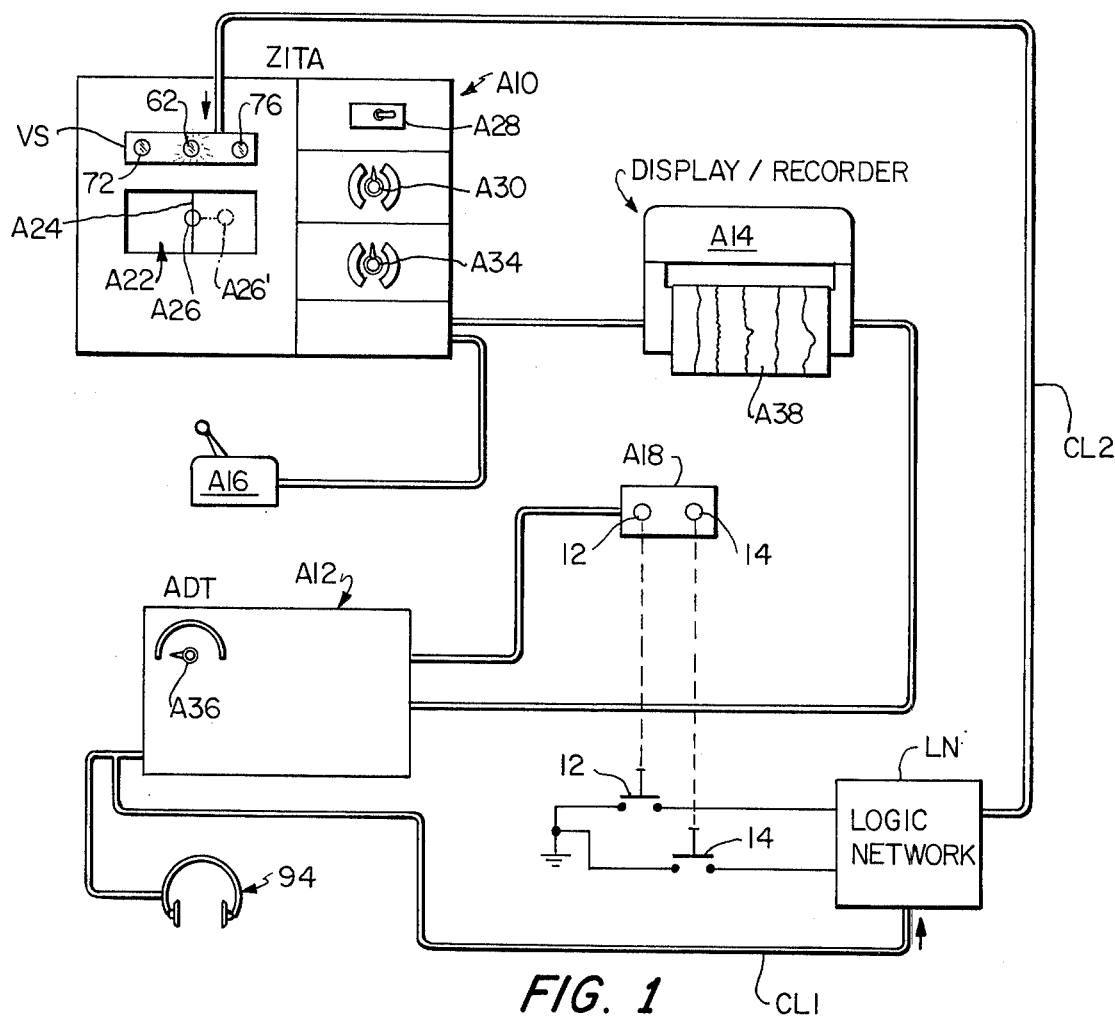

METHOD FOR MEASURING TASKS AND MEANS FOR GENERATING COORDINATED AUDIO-VISUAL STIMULI AND ERROR INDICIA FOR SAID SECONDARY TASKS

FIELD OF INVENTION

This invention relates to diagnostic testing methods and apparatus for accomplishing same and more particularly to improvements in the methods and apparatus of applicant's prior U.S. Pat. No. 3,579,865, issued May 25, 1971 which is incorporated by reference herein. The improved method and apparatus is particularly well adapted to the diagnosis of mental illness and disabilities in persons of all ages, with and without specific sensory impairments and/or disfunctions and disabilities.

BACKGROUND OF THE INVENTION

The basic apparatus utilized in the method of the present invention includes a Zero Input Tracking Analyzer, herein after referred to as a ZITA and an Auxiliary Distraction Task device hereinafter referred to as an ADT. These two devices impose primary and secondary tasks, respectively, on a person being tested as generally described in applicant's above-referenced prior patent.

The response of the person under test over a given time interval is scored and recorded as an index of the ability of that person to perform various tasks with and without the imposition of stress. In short, the ability of a given person to perform in any specified environment can be determined.

As more experience with the use of ZITA/ADT diagnostic testing was gained, it became increasingly apparent that the possibility of diagnosing human abnormalities and disfunctions such as hypoactivity, hyperactivity, minimal brain disfunction (MBD), schizophrenia and aphasia as well as the response of persons so diagnosed to corrective treatment would and could be an invaluable aid to such treatment. Thus, a crying need in the art could possibly be solved by the use of ZITA/ADT analysis.

Where the ADT stimulus was merely the random generation of high and low tones to which the tailored responses were, respectively, first and second extreme positions of a control stick, to be performed simultaneously with the primary tracking task imposed by the ZITA, it became readily apparent that reliable results could not be achieved. An ADT format which would universally apply to both young children (under 5 years of age, for example) pre-teen and teen-age children and adults, and both unhandicapped and handicapped persons in all of the foregoing categories was sorely needed.

OBJECTS OF THE INVENTION

It is therefore, an object of the present invention to provide an improved method of psychological testing which is readily adaptable to a wide variety of diagnosis on both normal and handicapped persons.

It is another object of the present invention to provide a universally applicable format of auxiliary distraction tasks for ZITA/ADT psychological testing methods.

Still another object of the present invention is to provide a new and novel means for generating instruction stimuli for auxiliary distraction tasks in the improved psychological testing methods of the present invention.

These and other objects of the invention will become more fully apparent with reference to the following specification and drawings which relate to a preferred embodiment of the present invention.

BRIEF DESCRIPTION OF THE DRAWINGS

FIG. 1 is a schematic of a ZITA/ADT testing means including the auxiliary distraction task improvements of the present invention;

FIG. 2 is a function table illustrating the interrelationship of auxiliary distraction task stimuli, time and response error.

SUMMARY OF THE INVENTION

Figure 3:
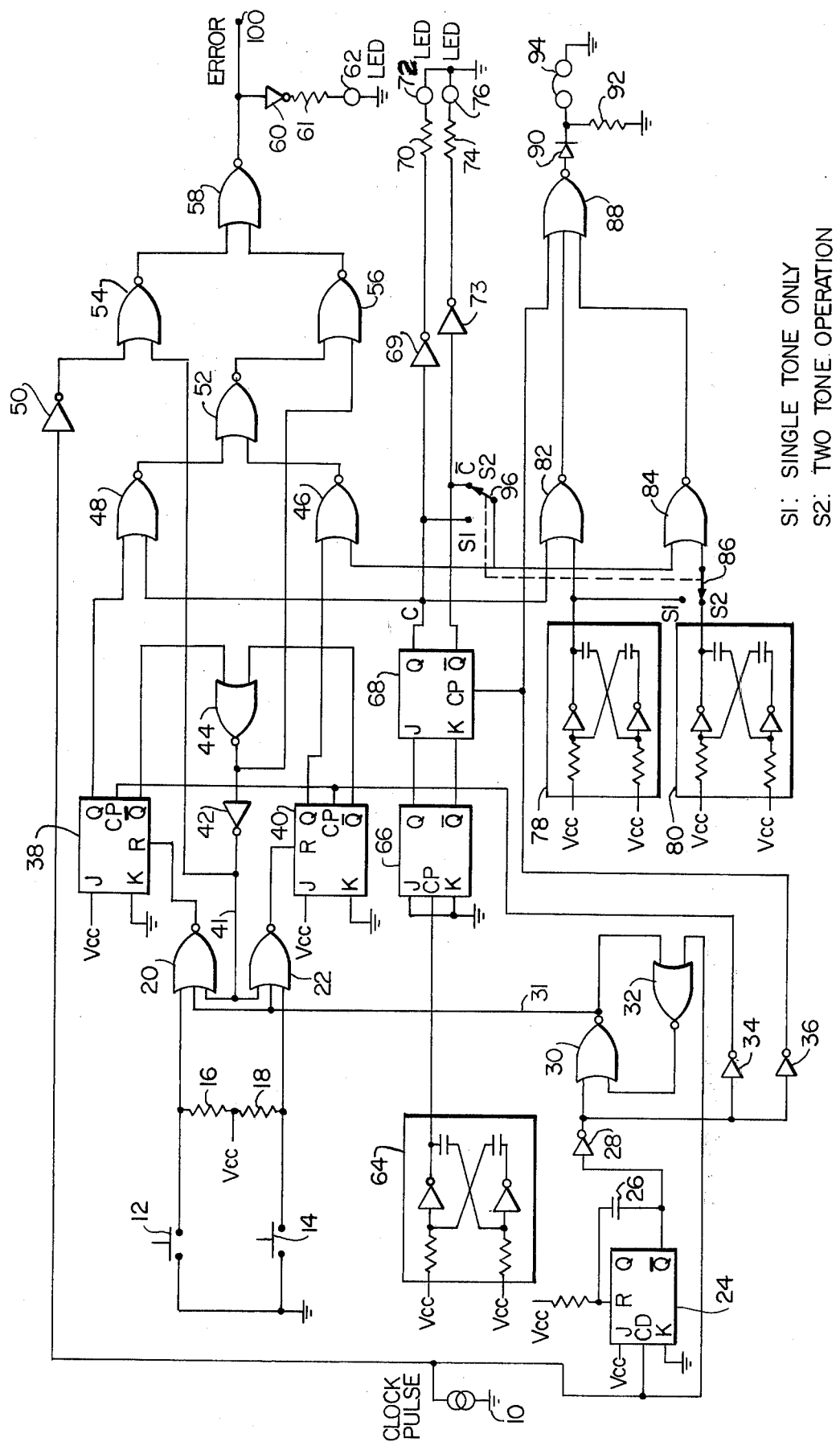
FIG. 3 is a schematic of a logic network which effectuates the auxiliary distraction task format of the present invention.

This inventive method of psychologic testing provides a means for quantifying the effects of stress on a man's tracking performance. The equipment used in the ZITA method, which is the primary task, has three basic components, the signal processor, the error analyzer and the display/recorder unit. The ZITA equipment provides a one dimensional tracking task for the operator in which he is required to centralize a spot of light in a display window. A display/recorder records control movements, integrated error, and rectified error, and these are permanently recorded. The operating cycle is indefinite, but the integrated error from which the means modular error for each cycle is readily derived, resets to zero in time cycles. The ZITA equipment can be used with various operator control stick devices. The uniqueness of ZITA resides in the fact that there is no external input inherent in the system. The operator has to null only his own error from his previous response which is initially propagated by his first initial response. ZITA, as a primary task or as a sole task, thus provides an unambiguous and reliable task, can accommodate different levels of stress, and has a simple and permanent read out.

The auxiliary distraction (secondary) task is intended to provide a simple, standardized psychomotor task which may be used alone or as a secondary task in combination with the primary task of the ZITA equipment to produce "distraction stress" in subjects operating the ZITA/ADT equipment.

In the ADT equipment the subject is provided with head phones for receiving discrete high and low beeps or tones which instruct the subject to operate a left and right control button, respectively. The high and low tones are respectively accompanied, simultaneously, by discrete visual light pulses at the left and right of the display window of the ZITA equipment.

An acceptable time frame for response to the left and right distraction task instruction stimuli is built into the system such that an incorrect response or a tardy response to these stimuli result in an "error", which error is detected by the ADT system and visually indicated by an error lamp centrally located with respect to the display window of the ZITA equipment.

Means is also provided to convert the ADT system to produce and detect errors resulting from a single instruction stimulous, i.e., an audible beep, visual pulse single button response as opposed to the dual ADT functions described above.

Such flexibility permits meaningful psychological testing of very young children (less than 5 years of age) for hypoactivity, hyperactivity, minimal brain disfunction, schizophrenia and the like.

The visual stimuli are provided by placing the lamps emitting the pulses of light such that no eye movement is actually required by the subject to sense and respond to these stimuli while performing the primary tracking task on the ZITA equipment.

The audible and visual stimuli from the ADT equipment are emitted at regular intervals in random modes, i.e., high and low, left and right, are unpredictable.

The primary tracking task on the ZITA equipment is performed by the subject with one hand by means of a control stick while the other hand manipulates either a two-button or single button response device depending upon whether the ADT equipment is constrained to the dual or single mode of secondary task stimuli.

Stimuli, responses and errors of the ADT are available for simultaneous display on the same display/recorder with the ZITA results.

DESCRIPTION OF THE PREFERRED EMBODIMENT

Referring in detail to the drawings and with particular reference to FIG. 1, there is shown the equipment embodying and for performing the method of the present invention, including a ZITA unit A10, an ADT unit A12 and a display/recorder A14.

A control unit A16 is manipulatable by the test subject, for example, with his right hand to perform a primary tracking task on the ZITA unit A10 while a control unit A18, comprising push button switches 12 and 14 (to be hereinafter more fully described) is manipulatable by one or two fingers of the subject's left hand in response to the command stimuli from the ADT unit A12 which are transmitted to the test subject by head phones 94 and signal lamps 72 and 76, as will also be further described hereinafter with reference to FIG. 3.

The command stimuli (high and low tones) applied to the headphones 94 are also applied to a logic network LN via a control line CL1 and thence via a control line CL2 to a visual signal lamp means VS comprising the signal lamps 72 and 76 and an error lamp 62, all mounted in close proximity to the display window or screen A22 in the ZITA unit A10.

The signal lamps 72 and 76 are left and right signals, respectively, corresponding to high and low signal tones in the headphones 94 and are respectively located at the left and right sides of the screen A22 in the ZITA unit A10. The error lamp 62 is substantially centered on the upper boundary of the screen A22.

The ZITA unit A10, is a compact unit containing all of the necessary equipment to carry out the primary task, which is a tracking task. A screen A22 is the visual presentation to the test subject with a grid line A24 in the center thereof to provide a central or zero position. A light spot A26 is movable in one dimension across the screen A22 and controlled by the test subject via control unit A16. The spot A26 is shown in unbroken lines in a zero position, and in a rightwardly displaced position by phantom line spot A26. The test subject would then manipulate the control unit A16 to the left in order to move the light spot from its position A26 toward the zero position A26. To make the centering of the spot A26 more difficult and to vary the type of task that may be administered, different types of controllers A16 may be used. The first type of controller that can be used is the standard or "proportional" type which gives a smooth variation of control. A second and preferable type of control that may be used is the "bang-bang" or "switching-type" that has three positions thereon, that of left, zero, or right control settings. With the latter type of switch, the "bang-bang", an additional control A28 is provided on the ZITA unit whereby a switch can be operated to change the "bang-bang" type of switch from a two position, left and right, to a three position, left, zero, and right, type of switch to thereby provide another variable in the tracking function to increase the difficulty thereof.

In addition to the variation of the type of switch that may be used in the controller, and the manner in which its operation may be modified by the switch A28, provision is also made to modify the command execution carried out by the spot A26 in response to stick movement of the controller A16. This further variation is a choice of response either in velocity or acceleration by means of switch A30. For example, if acceleration is the type of control command to be used in a given test, the switch A30 would be turned to the right thereby offering a wide range of "stiffness", which is a measure of angular acceleration, available in this type of test. Similarly, if the control command is to be a function of velocity, the switch A30 is moved to the left. A wide range of lag or lead times may be introduced into the response by moving the switch A34 to the right or left.

The ADT unit A12 is primarily a sound generator producing two sounds, e.g., consisting of a "ping" or a "pong", which are the stimuli to be presented to the test subject. The first, or "ping", denotes a short pulse of high pitch sound, while the latter, or "pong", denotes an equal length pulse of a tone of lower pitch. These sounds are presented to the test subject by means of head phones 94. The test subject is provided with the control unit A18 for the ADT, which requires him to move the stick thereof either forward or backward depending upon which of the sounds have been designated forward or backward.

The subject is instructed to use the ADT control unit A18 by pressing the left switch button 12 in response to high pitch tones in the earphones and/or a visual pulse in the left hand signal lamp 72 and by pressing the right hand switch 14 in response to low pitch tones in the earphones 94 and/or visual pulses in the right hand signal lamp 76.

The stimuli of the ADT are presented in a random order but at predetermined intervals, which intervals can be set by interval program means such as a switch A36 or other suitable programmer such as a record. The ADT can normally be set for an interval of 2 seconds between stimuli, but other regular intervals or variable intervals may also be introduced.

The display/recorder A14 can be anyone of a number of commercially available units that provides a graph type of record A38 which provides the display of what the test subject is doing during the course of his tasks, and also provides a permanent record of that task. The ZITA unit A10 and its controller A16 are interconnected with the display/recorder A14 so that when the test subject attempts to track the spot A26 properly, the results are recorded on the graph A38. The graph A38 will preferably provide a record of the movement of the stick on the controller A16, the tracking of the spot A26 with respect to the zero grid line A24, the error in the tracking function, and the slope of the integrated error or cumulative error during the course of the performance of the task.

Similarly, the ADT unit A12 is interconnected with the display/recorder A14 so that the subject's manipulation of the control unit A18, in response to the sound stimuli, can be presented on the graph A38 with the record of the ZITA test. The graph A38 will preferably record from the ADT test, the input signal or stimuli presented to the test subject, and the test subject's response to the stimuli. Thus, the performance of the test subject with regard to the primary or ZITA task, and the secondary or ADT task can be presented in an easily handled form.

The operation of the ZITA unit A10 is fully described in applicant's prior U.S. Pat. No. 3,579,865 of May 25, 1971.

The improved method and apparatus to which the present invention is directed concerns the ADT stimuli and a control circuit for generating and correlating the ADT stimuli.

Basically, referring to FIG. 2, the interrelationships of the AUTO INPUTS (generated secondary task stimuli) and the RESPONSE of a test subject are indicated in a matrix in which 0 indicates the non-occurrence of an input or response and 1 indicates an occurrence of an input or response in the dual-tone, dual-visual stimuli mode of operation of the ADT unit A12.

For the alternate single tone, single visual stimulus mode, a response button is pushed for any given stimulus and the only "error" to be recorded is a lack of response to the stimulus within the given time limit between recurrences of any given stimulus, i.e., failure to actuate one of the push buttons 12 and 14.

Referring now to FIG. 3, the ADT stimulus generating and error detecting circuit (which includes the logic circuit LN of FIG. 1) is shown as including a block pulse generator 10, of any suitable type known to those of ordinary skill in the art, which generates a stream or train of positive going clock pulses of standard logic level. The typical rate of these pulses is on the order of 0.5 to 5 seconds between pulses.

This clock pulse train is sent to three different circuits. It is sent to a pulse inverter 50 so that the "off" time (time between pulses) is established as the time during which errors may be made and detected. The clock pulses are sent to a pulse stretching multivibrator 24 which is constructed from a standard J-K flip flop with a capacitor 26 connected from its reset terminal R to one of its output terminals $\overline{Q}$. The clock pulse is also sent to a pair of standard NOR gates 30 and 32 which are cross-connected to act as a "set/reset" flip-flop, so that the output pulse on line 31 is held low during the time following the circuit start-up by each clock pulse. A multivibrator 64 comprising a pair of cross coupled inverter gates, produces a symmetrical square wave at a supersonic frequency (too high to be heard). Second and third multivibrators 78 and 80, respectively, are constructed and operate in an identical manner except that their parameters are chosen to create a pair of audible tones at different frequencies. The second multivibrator 78 produces a high audio tone while the third multivibrator 80 produces a low audio tone. These two tones are commanded and directed to head phones 94 by means of NOR gates 82 and 84, with the high audio tone fed through NOR gate 82 and the low audio tone fed through NOR gate 84.

First and second selector switch means 86 and 96 are operated together, in gang, so that equivalent circuit operation may be obtained with only a single high tone, as produced by the second multivibrator 78 which tone may be used to energize the head phone 94. The said two NOR gates 82 and 84 bring forth the high and low (or single high) audio tones to two inputs of a three input NOR gate 88 and thence to the head set 94 through a diode 90 and load resistance 92. Diode 90 and resistance 92 are used so that transient signal energy generated by the inductance of the head phones 94 will not harm the NOR gate 88.

The clock pulse, as lengthened by the multivibrator 24, is inverted by the inverter gate 28 and again inverted and isolated by two inverter gates 34 and 36. Inverter 36 performs two functions, namely, it drives the third input of the NOR gate 88 and the clock pulse terminal of a J-K flip-flop 68.

When the output of the inverter 36 is low, it enables the NOR gate 88 to pass the high and low (or single high) audio tones to the head set 94. This condition only occurs for a short time after the clock pulse has initiated the sequence. The timing of the tone burst from the stretcher 24 is set by capacitor 26 and is typically on the order of 50 milliseconds. As previously stated, the multivibrator 64 is oscillating at a supersonic rate and its speed of transition is cut in half by the action of a J-K flip flop 66 having its clock pulse terminal CP driven by the output of the multivibrator 64 and the resulting output of the flip-flop 66 is converted into a rapid series of 0's and 1's at the outputs Q and $\overline{Q}$ thereof.

The gate output transition from the inverter 36 enters the J-K flip-flop 68 at its clock pulse terminal CP and it is literally pure chance at that point whether the two inputs J and K of the flip-flop 68 will possess a 0-1 combination or a 1-0 combination.

Hence the gating pulse from the inverter 36 places a random function at the outputs Q and $\overline{Q}$ of the flip flop 68. The "C" output (Q) for example can be either high or low and "$\overline{C}$" output ($\overline{Q}$) can be either low or high. This condition will be established at the time of the clock pulse and will remain the same until the next clock pulse is received, at which time a new random sequence will be selected for the output busses C and $\overline{C}$. When C is low for example and $\overline{C}$ is high, the high audio cone is selected by the NOR gate 82 and transferred out to one input of the NOR gate 88. Conversely, when "$\overline{C}$" is low, the low tone is transferred out by NOR gate 84 to another of the inputs of NOR gate 88. These "low" states are inverted in inverters 69 and 73 driven by C and $\overline{C}$, respectively and they thereupon are selectively directed to two LED indicator diodes 72 and 76, respectively, via the current limiting resistors 70 and 74, respectively, in series with the said diodes. The inverter 69 feeds resistor 70 and LED indicator 72. When the high tone is being sent and, "C" is "low" the output of the inverter 69 is "high" and LED 72 is energized. The LED 72 is the left hand visual stimulus in FIG. 1. Conversely when condition of the buss C is established at the "low" logic level, the inverter 73 output is "high" and the LED 76 is energized, indicating that the lower of the two audio tones is being sent out. The LED 76 is the right hand visual stimulus in FIG. 1.

Thus a random selection of 50 millisecond bursts of high or low audio tones are sent to the head phones 94 every time a clock pulse is emitted from the generator 10. When the selector switch means 86 and 96 are thrown from the S2 position to the S1 position thereof, only the 50 millisecond high tone is sent out when a clock pulse is emitted.

The push button means 12 and 14 are provided so that the human test subject may react to the audio and/or visual stimulus. Push button 12 is associated with the "C" buss (the high audio tone) and push button 14 is associated with the "$\overline{C}$" buss (the low audio tone).

When the high audio tone buss is heard and/or the left hand LED 72 pulses, the operator is supposed to press push button 12 before the next clock pulse to avoid making an error. If he pushes button 14 instead or if he does nothing, this counts as an error and is so indicated at output terminal 100 and by an LED 62 via its current limiting Resistor 60. Conversely when the low tone is heard and/or the right hand LED 76 pulses, the operator must depress push button 14 in proper time or it will be counted as an error in a similar manner.

This process occurs as follows:

Push button 12 is depressed which grounds a normally "high" input of a NOR gate 20. The input 31 to this NOR gate 20 will be low shortly after the tone burst starts by the action of the cross coupled NOR gates 30 and 32. When buss 41, which comprises common inputs for the NOR gates 20 and 22, is also "low", the output of NOR gate 20 can go high indicating that the operator has decided to push the left button 12, in response to perception of a tone and/or visual stimulus. When this pulse at the output of NOR gate 20 goes high it is applied to the reset terminal R of flip-flop 38; and if flip flop 38 is in a receptive state, by the action of inverter 34 at its clock pulse terminal CP, the flip flop 38 will change state. Then, the output to NOR gate 48 from the "Q" terminal of flip flop 38 will go high. By the same token flip-flop 40 will be pulsed from inverter 34 but it will not change state because the corresponding action via push button 14 did not occur. Thus, after the two flip-flops are pulsed by the output pulse from the inverter 34 the inputs to NOR gate 44 are "low" and its output is high until a button is pushed. This output is inverted by the inverter 42 and is presented as an "enabling low level" input to the input NOR gates 20 and 22. When the flip-flops 38 and 40 are forced to change state by the output pulses from the inverter 34, this condition remains, unless a button 12 or 14 is pushed.

When either button 12 or 14 is pushed, the corresponding flip-flop 38 or 40 changes state and the output to NOR gate 44 goes low, the output of inverter 42 becomes high and all further button pushing is locked out of the circuit.

When the operator correctly choses a push button 12 or 14 and the corresponding flip-flop 38 or 40 has changed state, this action is compared in NOR gate 48 (for high tones, left lamp 72 and push button 12) and NOR gate 46 (for low tones, right lamp 76 and push button 14). If the operator was correct in each case, the output of the proper NOR gate 48 or 46 will go high and this condition signals that no error has been made by the resulting action of NOR gate 52, 56 and 58.

When an error in button pushing is made, NOR gate 48 is activated for a high tone, left lamp mistake and NOR gate 46 is activated for a low tone, right lamp mistake. NOR gate 48 accepts a "low level" from buss "C" and when flip flop 38 changes state, a low level is sent to the other input of NOR gate 48 and the no error condition is signalled by the output of NOR gate 48 going high. At the same instance NOR gate 46 has one "high" input from buss $\overline{C}$ (when 2 tones are being used) and another high input from the flip-flop 40.

The converse process holds when no error is made in signalling with push button 14 a response to a low tone and/or right lamp 76. When no error is made, one input to NOR gate 52 is low and the other input is high and its output, therefore, is low. NOR gate 56 accepts this low input from NOR gate 52, but its other input is high, via NOR gate 44 until a button 12 or 14 is pushed. Then, this other input will go low.

As long as no error is made both inputs to NOR gate 56 will be low and its output will be high.

When an error in button pushing is made, the output of NOR gate 58 goes from high to low and this is signalled by a drop in voltage at error buss 100 from VCC to low. Inverter 60 converts this signal to a high when an error is made, and operates an LED error indicator 62 via a current limiting resistor 61 in series with the output of the inverter 60. When the wrong button is pushed, the error indication lasts from the time of the error until the next clock pulse starts another sequence. When a "no-button-push" error is made the error is signalled only for the duration of the next clock pulse, due to the combined action of an inverter 50 and a NOR gate 54.

With the foregoing description of the various interrelationships of the several components of the ADT network of FIG. 3, the said components may be further identified in the following functional groups:

I. Pushbutton Selection Input Data Means, comprising:
input NOR gates 20 and 22;
selection responsive flip-flops 38 and 40;
synchronizing inverters 36 and 42, the latter responsive to a NOR gate 44 driven by the $\overline{Q}$ outputs of the selection responsive flip-flops 38 and 40; and
the NOR gate flip-flop 30, 32 which drives common inputs of the input NOR gates 20 and 22.

II. Clock Generating And Timing Means, comprising:
clock pulse generator 10;
off time interval determining inverter 50 for enabling one input to an error detecting circuit means (NOR gates 52, 54, 56 and 58); and
clock pulse stretching multivibrator 24 driving NOR gate flip-flop 30, 32 and inverters 34 and 36 which synchronize the selection flip-flops 38 and 40, tone selector and lamp driver flip-flop 68 and the NOR gate 88 which drives the headphones 94.

III. Random Stimpli Selection Generating Means, comprising:
high frequency multivibrator 64 driving flip-flops 66 and 68, the latter driving the left and right signal lamps 72 and 76 and the enabling NOR gates 82 and 84 of the high and low tone generating multivibrators 78 and 80;

IV. The Tone Generators 78 and 80;

V. Stimuli Selection To Push Button Selection Comparator Means, comprising:
NOR gates 48 and 46 responsive to the high tone — left lamp 72 — left push button 12 and low tone — right lamp 76 — right push button 14 combinations respectively, each driving one input of a comparator output NOR gate 52 which in turn drives one input of right-wrong switch selection NOR gate 56, the latter having its other input terminal driven by the output of the common $\overline{Q}$ enabled NOR gate 44 of the selection flip-flops 38 and 40;

VI. Failure To Timely Select Push Button In Response To Stimuli Detection Means, comprising:
  NOR gate 54 driven at on terminal by the direct clock pulse inverter 50 and at the other terminal by the output of the inverter 42, this output being the inverted output of the common output NOR gate 44 of the selection flip-flops 38 and 40; and
VII. Error Detection Correlation Means, comprising:
  NOR gate 58 driven by the outputs of the NOR gates 54 and 56 to drive the inverter 60 and illuminate the error lamp 62 therethrough.

The foregoing groups of elements V, VI and VII comprise an error detecting network for the ADT circuit.

The novel ADT stimulus generating means described above provides a variety of command stimuli in both the audible and visual modes as well as the selective feature of single or dual commands in each mode. The correlation of command stimuli to the actual response function of the person being tested is reliably monitored to provide both a visual error indication and a voltge change indicative of that error for recording purposes.

The multiple modes of the various stimuli have been found to be extremely valuable in utilizing the ZITA-/ADT method of testing as a diagnostic tool to predict and monitor changes in hypoactivity, hyperactivity, minimal brain disfunction, schizophrenia and other mental disorders in children and adults of all ages and with varying physical impairments of the human sensory systems.

The single tone, single visual stimulus mode is particularly advantageous in the testing of very young children (under 5 years of age for example) where the mental sophistication of the person tested is relatively unequipped to perform more than a simple single secondary task commanded by the ADT unit A12.

The high and low audible tone — left and right visual stimulus mode adapts to all other age groups and provides a sufficient variety of stimuli to permit even handicapped persons, such as those with specific hearing or sight defects, to be tested with reliable data resulting.

The visual stimuli are placed such that peripheral vision permits the detection of the stimuli with optimally minimum distraction from the primary tracking task required by the ZITA unit A10.

The error lamp 62 further improves the reliability of the resulting data in that persons with sufficient comprehension and mental ability can profit by this indication while those with specific mental disabilities will tend to show either little or no change or more distraction depending upon their disability.

As can be readily seen from the foregoing specification and drawings the present invention satisfies a long felt need in the art for a simple and reliable diagnostic tool for the diagnosis of mental illness and disability as well as the analysis of performance of persons under stress conditions.

The present invention may be modified as would occur to one of ordinary skill in the art without departing from the spirit and scope of the present invention.

I claim:

1. Means for generating multiple modes of command stimuli for dictating performance of specific tasks and monitoring the correctness of responses thereto, comprising:

clock pulse generating and timing means providing clock pulses and timing signals at regular predetermined intervals;
  random stimuli selection signal generating means enabled by said timing signals from said timing means to provide first and second stimuli selection signals at regular intervals and in random sequence;
  first and second signal generating means providing first and second audio output frequencies, respectively;
  gate means having inputs driven by said timing means, said first and second audio outputs and said first and second random stimuli selection signals and selectively enabled thereby to pass said first and second audio outputs in random sequence at regular intervals;
  audio output means in circuit with said gate means driven by and providing first and second discernible tones in response to said audio output frequencies;
  first and second light emitting means in circuit with said random stimuli selection signal generating means energized, respectively, by said first and second stimuli selection signals and in synchronous correlation, respectively, with said first and second discernible tones to produce first and second visual stimuli such that related ones of said tones and said visual stimuli provide a dual command stimulus for a given task to be performed;
  response means comprising first and second input devices to be actuated in response to and in correlation with said first and second discernible tones and/or said first and second visual stimuli;
  detector circuit means enabled by said timing means and responsive to the actuation of said first and second input devices to provide first and second response signals, respectively;
  error detecting gate means having respective inputs enabled by said clock pulse means, said first and second random selection signals and said first and second response signals providing an error output in response to errors comprising a lack of actuation of either of said input devices within said regular predetermined interval between said clock pulses and said tones and/or visual stimuli and in response to actuation of said input devices out of correlation with said tones and/or visual stimuli; and
  indicating means responsive to said error output to indicate the occurrence of a said error.

2. The invention defined in claim 1, wherein the said generating and monitoring means further includes selector means selectively precluding one of said first and second signal generating means and a correlative one of said first and second random stimuli selection signals from driving, respectively, said audio output means and the correlative one of said first and second light emitting means to provide a single tone, single visual stimulus mode of operation.

3. The invention defined in claim 1, wherein said first and second light emitting means and said indicating means respectively comprise light emitting diodes.

4. The invention defined in claim 1, in combination with a zero input tracking analyzer having a display screen for testing persons in the performance of primary and secondary tasks, wherein, said first and second light emitting means are respectively mounted on said analyzer adjacent the left and right peripheral boundaries of said display screen to permit observation of said first and second visual stimuli within the immediate peripheral vision of a person being tested.

5. The invention defined in claim 1, in combination with a zero input tracking analyzer having a display screen for testing persons in the performance of primary and secondary tasks, wherein, said error indicating means comprises a third light emitting means mounted on said analyzer immediately adjacent the periphery of said display screen.

6. The invention defined in claim 4, wherein said error indicating means comprises a third light emitting means mounted on said analyzer immediately adjacent the periphery of said display screen intermediate said first and second light emitting means.

7. The invention defined in claim 4 wherein said first and second input devices are positioned to the left and right of one another in correlation to the left and right positions of said first and second light emitting devices with respect to said display screen to provide a directional correlation between said visual stimuli and said input devices.

8. The invention defined in claim 7, wherein said error indicating means comprises a third light emitting means mounted on said analyzer immediately adjacent the periphery of said display screen intermediate said first and second light emitting means.

9. A method for measuring the performance of a human operator, or the difficulty of a task to be performed by a human operator, or distracting effects of surrounding environment, comprising:
  a. providing a movable and visible tracking spot and a reference position therefor;
  b. causing movement of the spot solely in response to application or control commands from a human operator, whereby there is no other deliberate input causing movement of the spot;
  c. providing an auditory stimulus of at least one tone and simultaneously providing at least one visual stimulus within the peripheral vision of the human operator adjacent the movable and visible tracking spot;
  d. supplying at least one correlated control response from a human operator for each said tone and/or visual stimulus;
  e. presenting said at least one tone and visual stimulus at regular intervals;
  f. detecting at least the presence or absence of said control response;
  g. providing a visual indication of the absence of said response at a position adjacent to the movable and visible tracking spot for observation by and within the peripheral vision of the human operator; and
  h. displaying and recording the occurrences in the foregoing steps for comparison therebetween.

10. A method for measuring the performance of a human operator, or the difficulty of a task to be performed by a human operator, or distracting effects of surrounding environment, comprising:
  a. providing a movable and visible tracking spot and a reference position therefor;
  b. causing movement of the spot solely in response to application or control commands from a human operator, whereby there is no other deliberate input causing movement of the spot;
  c. providing audible stimuli of first and second tones and first and second visual stimuli in random sequence and at regular predetermined intervals, with said visual stimuli positioned within the peripheral vision of the human operator adjacent the movable and visible tracking spot;
  d. supplying first and second control responses from a human operator, correlated, respectively, with said first tone and first visual stimulus and with said second tone and second visual stimulus;
  e. detecting the lack of response of the human operator to said stimuli within said predetermined time interval or the improper correlation of a response within said interval to said stimuli;
  f. providing a visual indication of said lack of or said improper correlation of a response at a position adjacent to the movable and visible tracking spot for observation by and within the peripheral vision of the human operator; and
  g. displaying and recording the occurrences in the foregoing steps for comparison therebetween.

11. The method of claim 10 wherein said first and second control responses are in a left and right sense, respectively, and wherein said first and second visual stimuli are provided to the left and right, respectively, of said movable and visible tracking spot for observation by and within the peripheral vision of the human operator to provide a directional correlation between said visual stimuli and said control responses.

* * * * *